United States Patent [19]
Weissman

[11] Patent Number: 5,788,492
[45] Date of Patent: *Aug. 4, 1998

[54] PROSTHETIC DENTAL BRIDGE FOUNDATION

[76] Inventor: Bernard Weissman, 225 E. 48th St., New York, N.Y. 10017

[*] Notice: The term of this patent shall not extend beyond the expiration date of Pat. No. 5,575,651.

[21] Appl. No.: 751,139

[22] Filed: Nov. 15, 1996

Related U.S. Application Data

[63] Continuation of Ser. No. 327,269, Oct. 21, 1994, Pat. No. 5,575,651, which is a continuation-in-part of Ser. No. 281,397, Jul. 27, 1994, abandoned.

[51] Int. Cl.⁶ .................................................. A61C 8/00
[52] U.S. Cl. ...................................... 433/173; 433/177
[58] Field of Search ............................. 433/172, 173, 433/177, 178, 190, 191, 193, 209, 194

[56] References Cited

U.S. PATENT DOCUMENTS

| | | | |
|---|---|---|---|
| 3,748,739 | 7/1973 | Thibert | 433/173 |
| 4,516,937 | 5/1985 | Bosker | 433/173 |
| 5,052,928 | 10/1991 | Andersson | 433/172 |
| 5,052,930 | 10/1991 | Lodde et al. | 433/173 |
| 5,064,374 | 11/1991 | Lundgren | 433/172 |
| 5,219,286 | 6/1993 | Hader | 433/172 |
| 5,221,204 | 6/1993 | Kruger et al. | 433/173 |
| 5,460,526 | 10/1995 | Bosker | 433/173 |
| 5,567,155 | 10/1996 | Hansen | 433/172 |

*Primary Examiner*—Christopher A. Bennett
*Attorney, Agent, or Firm*—Barry G. Magidoff; Paul J. Sutton

[57] ABSTRACT

A module useful for forming a foundation for a dental prosthesis, the module including at least one each of (a) a post and (b) an extension unit, the post having a threaded end adapted to anchor the post into rigid dental materials such as tooth stubs or bone matrix, and a second retaining end for engaging the extension unit. The extension unit comprises an engaging end to engage the retaining end of the post, and one or two leaves extending from the engaging end transversely from the post. The engaging end is so sized and shaped as to maintain a sloppy fit with the retaining end of the post. The sloppy fit permits a minor, constrained degree of rotation of the extension unit with respect to the post. At least two such modules can be used to form the foundation for a rigid prosthetic dental bridge; at least one of the extending leaves on each module is so formed as to be capable of coupling with one of the extending leaves on a second such module. A pair of coupled such modules forms a prosthetic foundation in the mouth.

5 Claims, 9 Drawing Sheets

PROSTHETIC DENTAL BRIDGE FOUNDATION

This Application is a continuation of U.S. patent application, Ser. No. 08/327,269 filed Oct. 21, 1994 and now U.S. Pat. No. 5,575,651 issued Nov. 19, 1996, which is a continuation-in-part of U.S. patent application Ser. No. 08/281,397 filed Jul. 27, 1994 and now abandoned.

BACKGROUND OF THE INVENTION

1. Field of the Invention

The present invention relates to the construction of a dental implant structure, and especially to interconnected, adjustable modular implanted units to form the foundation for a rigid prosthesis and, in particular, to form the foundation for a rigid prosthetic dental bridge. In particular, the present invention relates to the construction of a modular dental prosthesis support foundation, fitted on the protruding heads of threaded post anchors implanted in bone. As a further embodiment, the present invention relates to the construction of an integrated rigid prosthetic dental bridge which is fitted on to protruding heads of threaded post anchors, and is readily removable for cleaning or repair or replacement.

2. Discussion of the Prior Art

Current techniques for placing a dental implant are time consuming, painful, and costly. Surgical intervention is required to place anchors in bone or tooth stubs. Multiple office visits, and dental laboratory services increase the cost and discomfort to the patient. The cost precludes the general population from obtaining the benefits of implant supported prosthesis, and lengthy healing periods result in patients being without teeth, or even a temporary prosthesis, for extended periods of time.

The most widely used implants are relatively large diameter, cylindrical hollow anchors, with internal and external threads. These anchors are surgically implanted in bone. The surgical procedure involves cutting the gum to expose the underlying bone and drilling channels into the bone. The anchors are then screwed into those pre-drilled channels and the gum is sutured, covering the implants. Healing must occur before supporting stumps can be screwed into the internally threaded hollow implants. Healing after implant, often requires about six to nine months, during which time the implants integrate within the bone. Once healing is complete, threaded stumps, to support a prosthesis, are screwed into the hollow anchors.

SUMMARY OF THE INVENTION

It is an object of this invention to repair failing key support abutments, to provide a strong, adjustable, modular superstructure for supporting a dental prosthesis, and to allow the placement of at least a temporary prosthesis and, in particular, a dental bridge immediately after the implantation of the foundation posts.

Another object of the present invention is to eliminate the disadvantages of current techniques by providing an effective means for constructing the foundation of a dental prosthesis and, in particular, a dental bridge without the need of surgery to expose the underlying bone, and thereby to eliminate the major cause of discomfort, inconvenience and substantial cost to the patient.

It is a further object of this invention to eliminate the delay of current techniques in the fitting of more permanent prostheses over implanted anchors.

Another object of this invention is to provide substantially normal masticatory function promptly after implantation, and lasting for a considerable length of time before a more permanent repair and solution need be effected.

The present invention comprises the use of relatively small diameter threaded anchor posts which can be directly threaded into bone matrix, and adjustable extension units for interconnecting the posts, and methods for using said units whereby the units are fitted to the implanted anchors and arranged into a rigid structure for use as the foundation of a dental prosthesis. Said structure then serves as the foundation for the construction, in situ, e.g. from self-curing moldable plastics and/or stock teeth, of a fixed or removable prosthesis. The foundation and prosthesis can be completed in the dentist's office, substantially immediately after implantation, without the surgery, dental laboratory services, multiple office visits, and delay in fitting a more permanent prosthesis required by current techniques.

This invention provides the means to replace a patient's missing teeth, especially the front teeth, with normal masticatory function immediately and concurrent with the implantation procedure.

As a further embodiment of this invention, there is provided a unitary prosthetic device forming an entire or partial complement of teeth or connecting only a few adjacent teeth, which can be readily removed for cleaning and then replaced by the user or dentist, and which is so formed that the prosthesis is rigidly interconnected together; this also permits ready replacement of teeth on implanted hollow screws or the like, and further provides great compressive strength for the interconnected unit with little or no lateral stress, or shear, being applied during function.

However, the use of this invention is not limited to the construction of a dental bridge. Screw anchors can be installed in areas where former anchors and key supporting teeth are deficient or lost. The small diameter of anchors permit their placement in narrow spaces between teeth, in thin bone cross sections, or in between implanted permanent anchors. Thus, temporary restorations can be supported during the lengthy healing and osseo-integration process of conventional permanent implants.

Other advantages of the invention will be obvious on reading the description.

DETAILED DESCRIPTION

In accordance with this invention, the foundation of a rigid prosthesis and, in particular, of a rigid prosthetic bridge is constructed of modular units, each modular unit comprising at least one of (a) a dental implant post and (b) an extension unit. Preferably, the post has a first tapered screw end, which is adapted to anchor the post, e.g. into bone matrix or a tooth stub, and a second retaining end, which is adapted to engage an extension unit which, preferably, is secured by a sloppy fit. Said sloppy fit permits a minor, constrained degree of rotation of the extension unit with respect to the retaining end of the post. The advantage of said sloppy fit is that each extension unit and each post head can be juxtaposed relative to each other so as to form a rigid interconnected bridge, constructed upon the implants, but can be easily dismantled and removed without substantial loss of bone ridge.

The extension unit of one modular unit is adapted to couple with at least one other adjacent modular unit. The extension unit is comprised of (i) at least one engaging means for engaging the retaining end of a post and (ii) no more than two leaves. When a post is engaged by an engaging means, each leaf extends from said engaging means in a direction transversely from the post and is selectable by length.

In the preferred embodiment, the posts are to be anchored in bone matrix or a prepared (pulpless) tooth stub. Each extension unit comprises an engaging means and, preferably, one or two leaves. In each module, the engaging means preferably, substantially surrounds the retaining end of the post and the cross section of the engaging means defines an aperture which provides a sloppy fit with the retaining end of the post, i.e., it is slightly larger than the cross section of the retaining end of the post. Preferably, the retaining end of the post and the cross section of the aperture of the engaging means have generally the same geometric shape. The size difference accommodates slight divergences in the sizes of the retaining ends of the posts and the apertures of the engaging means. The leaf or leaves extend from the engaging means in a direction transversely from the post and are selected by length. If necessary, the leaves may be cut to desired length; the leaves are corrugated to improve their strength. With the possible exception of the engaging means at the ends of each foundation, each engaging means is connected with two leaves and each leaf is coupled with another leaf or engaging means from another adjacent extension unit. Preferably the coupling is accomplished by the overlapping and clipping together of two corrugated leaves. Caps are then constructed by conventional means, for example, by molding, over each post. In the alternative, a single cap can be constructed over an anchor post coupled to an extension unit.

In another preferred embodiment, a spring loaded support skeleton, or cap, is fitted over the head of an anchor post, or an anchor post coupled to an extension unit, to serve as the foundation for the construction of a crown or prosthesis by conventional means. Caps can thus be fitted over each of a series of adjacent anchor posts of the foundation to complete a bridge.

In an alternative embodiment to this invention, the retaining end of the post may be of any shape wherein the engaging means substantially surrounds the retaining end of the post and the cross section of the engaging means defines an aperture providing a sloppy fit between the extension unit and the post.

In another embodiment of this invention, the retaining end of the post has an aperture or groove which engages the extension unit. In this case, the extension unit passes through the aperture or groove. The relative dimensions of the aperture or groove to the dimensions of any portion, i.e. engaging means, of the extension unit which engages said aperture or groove defines a sloppy fit. In this embodiment, a single extension unit can engage a plurality of serially adjacent posts. Furthermore, in this embodiment, any portion of the extension unit may serve as an engaging means. The crown foundation, e.g. a spring-loaded skeleton support foundation over a post head, can serve to retain the engaging means within the slot. The preferred extension unit is a bar having a certain limited flexibility that would enable it to follow the curvature of the mouth and to change direction between adjacent implanted posts, so as to form a continuous connector between the terminal posts in a chain of such implanted posts.

Most preferably, locking means are provided between the continuous bar and a locking cap, placed over and/or around the top portion of the post, so as to hold the bar in place relative to the post. A continuing succession of such locking means at the successive posts creates a relatively secure and unitary structure. The ends of the bar can be wrapped around, or otherwise locked onto, the two terminal posts. To further enhance the structural strength of the system, the entire combination of the adjacent locking caps and bar can be encased in a moldable, soft composition, which when hardened (as by curing) will enhance the rigidity of the structure. To further improve the structural strength of the encasing composition, a reinforcing coil can partially or completely surround the bar, and contain and be enmeshed within, the encasing composition. A series of individual teeth parts can then be formed and secured onto the rigid foundation by known means. The rigid foundation thus formed can be readily removed from and replaced upon, the implanted posts, to form a rigid, removable dental prosthesis. It is also possible to utilize a prepared tooth stub, together with adjacent implanted posts, as the basic support for the prosthesis.

In another preferred embodiment of this invention, two extension units extend generally parallel to each other and on opposite sides of two or more implanted posts, tooth stubs or prior existing prostheses. The consecutively placed implanted posts, tooth stubs or prior existing prostheses serve as a chain of anchors, generally referred to as anchored perpendicular support elements. The first said extension unit runs along the buccal side of the anchored perpendicular support elements and the second said extension unit runs along the lingual side of the anchored perpendicular support elements. The first and second extension units are crimped, clipped or otherwise made to engage each other so as to form engaging surfaces which substantially surround and engage each post or tooth, thus forming the foundation of the invention.

A combination of the teachings of this invention may be employed in the construction of a dental prosthetic bridge.

DESCRIPTION OF THE DRAWINGS

FIG. 12 is a magnified, partially sectioned, partial view of implanted dental posts of FIG. 11;

FIG. 13 is a magnified view of the outer portion of a dental post and locking means of FIG. 12a;

FIG. 14 is a side view of a portion of a connecting bar;

FIG. 17 is a top plan view of a cruciform-slotted dental post used in this invention;

Figures 6, 7, 10:
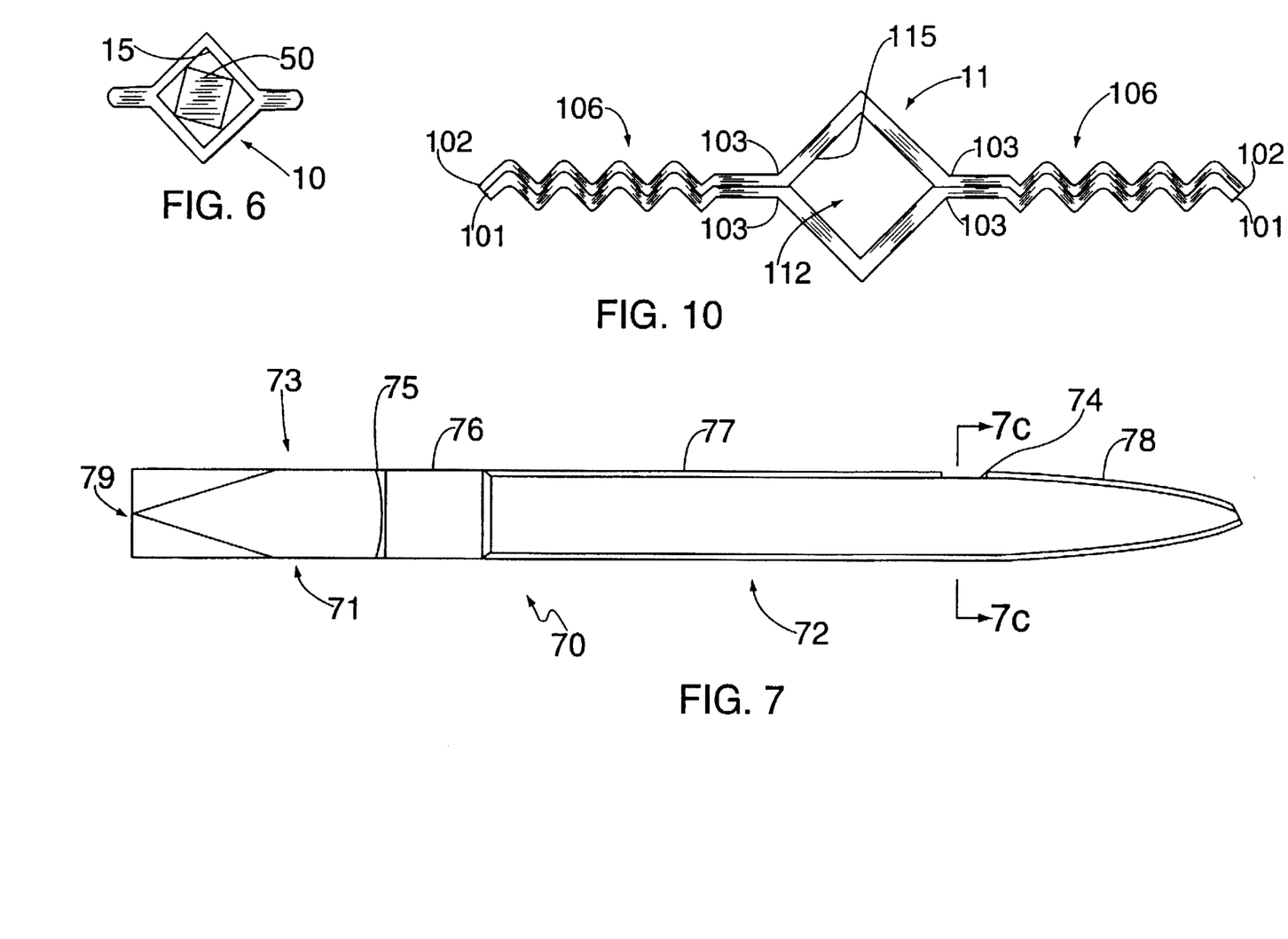
FIG. 6 is a plan view of an extension unit fitted over a post.
FIGS. 7 is an elevation view of a post.
FIG. 10 is a plan view of another embodiment of a series of extension units, formed in situ.
Figure 7A:
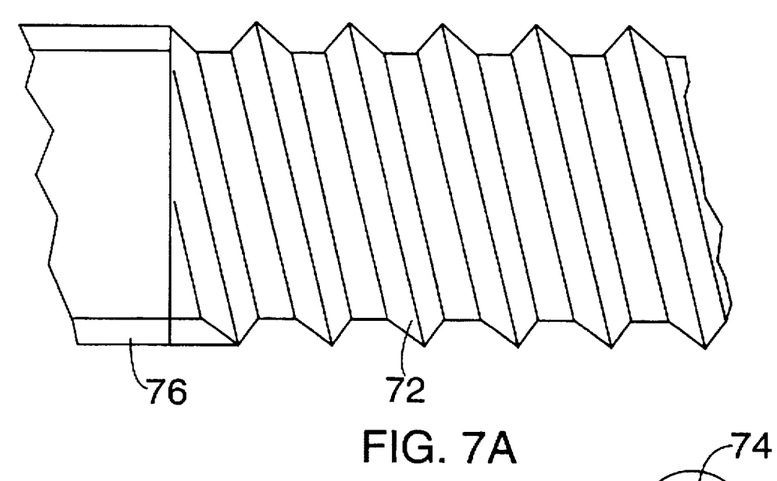
FIG. 7a is a detail elevation of the threaded end of the post of FIG. 7.
Figures 7B, 7C, 7D:
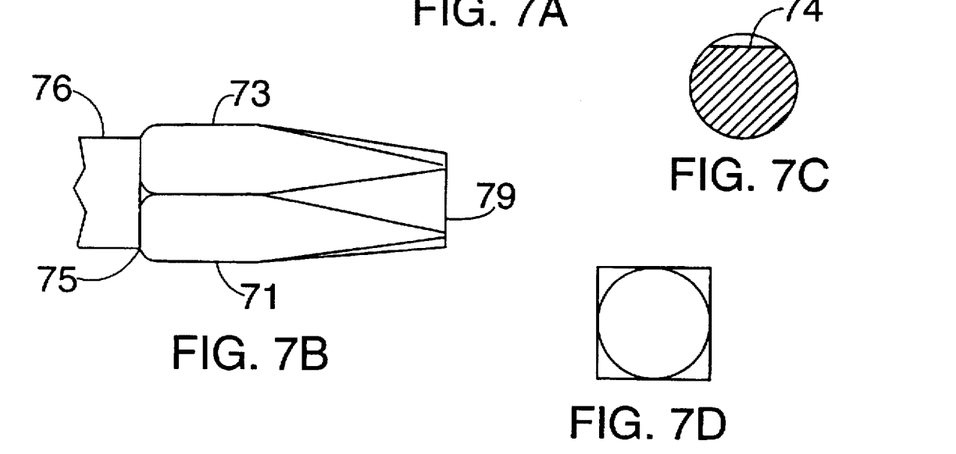
FIG. 7b is a detail elevation of the retaining head of the post of FIG. 7.
FIG. 7c is a cross section of FIG. 7, through line c—c.
FIG. 7d is a cross section of FIG. 7b, through line d—d.

Referring to the drawings, FIG. 7 shows a post, generally designated by the numeral 70, with one threaded screw end 72 for insertion into bone matrix, or a tooth stub, and a second retaining end 71 for retaining an extension unit. The retaining end comprises the head 73, neck 75 and shoulder 76. The threaded screw end includes the body 77 and the tail 78. The body is integral with the tapered tail. An anti-rotational facet 74 is cut into the body of the post adjacent to the tail, to prevent loosening of an implanted screw post. FIG. 7a shows a detail of the screw end 72 and FIG. 7b shows a detail of the retaining end 71. FIG. 7c is a cross section of the post at the level of the anti-rotational facet 74. FIG. 7d is a cross section of the retaining end of the post at line d of FIG. 7b. Each end can vary, and a post may be a combination of those variations. For example, the retaining end can be grooved.

Figure 1:
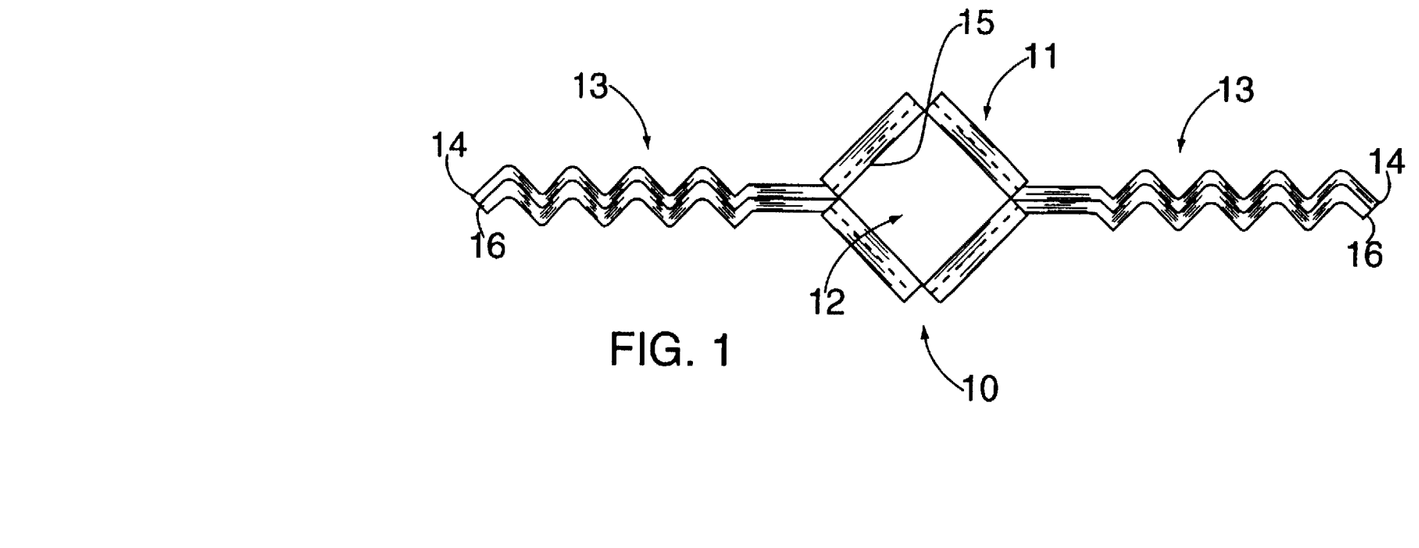
FIG. 1 is a plan view of one embodiment of an extension unit with two corrugated leaves.
Figure 1A:
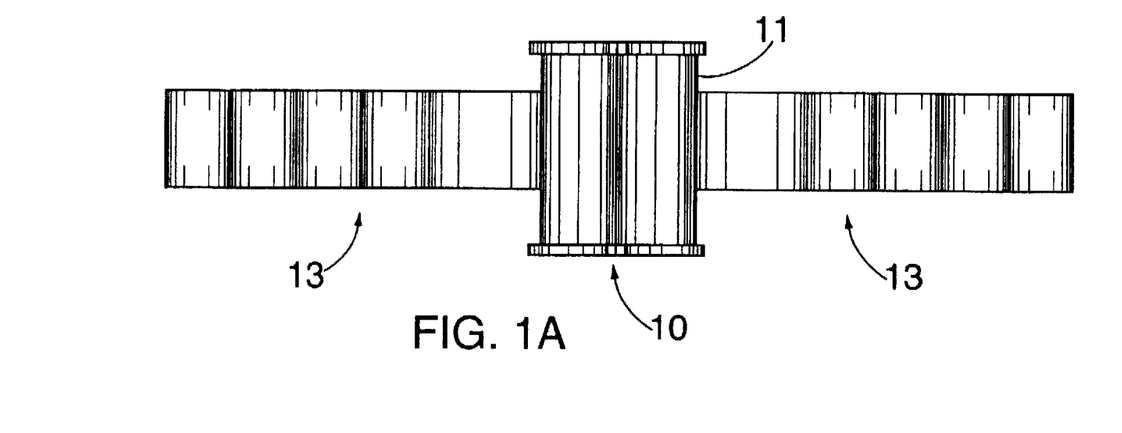
FIG. 1a is a side elevation view of the embodiment of FIG. 1.

FIGS. 1 and 1a detail an embodiment of an extension unit, generally designated by the numeral 10, with an engaging means, generally designated by the numeral 11, which is a rectangular tube, which in cross section defines a square aperture 12, and with two corrugated leaves 13 extending from the engaging surface. In the embodiment shown in FIG. 1, the extension unit 10 with an engaging means 11 is constructed in two halves 14 and 16 welded or otherwise rigidly secured together. In said embodiment the engaging means has an engaging surface 15, which defines a square aperture each side of which has a length of about 1.9 mm and engages a square retaining end, such as the retaining end 71 of the post 70 in FIG. 7, in which each side is slightly smaller than the aperture.

In the most preferred embodiment, the posts are solid and made of a titanium alloy. The screw end of each post is tapered and externally threaded, and contains an anti-rotational facet to prevent the loosening of the post. The posts are preferably from about 18 mm to about 22 mm in total length, with a head of about 5 mm in length, a shoulder of about 2 mm in length, a body of from about 6 to about 10 mm in length, and a tail. The shoulder joins the head at the neck. The shoulder is square, in this embodiment, for simplifying holding the post while driving the screw end of the post into bone matrix. The head is square in cross section with each side of said square having a maximum length of about 1.66 mm, the first 3 mm of the length of the head are tapered to the free end 79 of the head 73 which has a diameter of about 1.65 mm. The head 73 is wider than the shoulder 76 and joins the shoulder 76 at the neck 75 at an angle of 30°. The shoulder 76 is integral with the body 77 and the body 77 is integral with the tapered tail 78. The body and the tail are threaded. In the body, the thread has an outer diameter of 1.8 mm, an inner diameter of 1.5 mm, a pitch of 0.5 mm and a cutting angle of 90°. The anti-rotational facet 74 is a planar groove in the threaded body of the post adjacent to the tail. Said groove is 1 mm in length and parallel to a diameter of the post, the distance between said plane and said diameter being from 0.65 to 0.70 mm.

Figure 5:
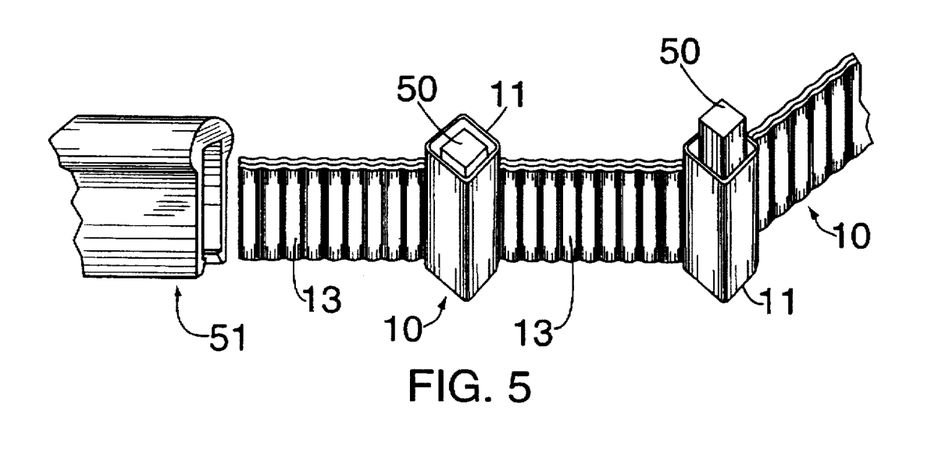
FIG. 5 is a side elevation schematic showing the interconnection of two modular extension units.

FIG. 5 schematically demonstrates the construction of the foundation of the dental bridge. In FIG. 5, one extension unit 10 is viewed in place over the retaining end 50 of a post, and another extension unit 10 is being placed over the retaining end 50 of another post. The leaves 13 of each extension unit extend from the engaging means 11 of each extension unit in a direction transversely from each post.

Figure 3:
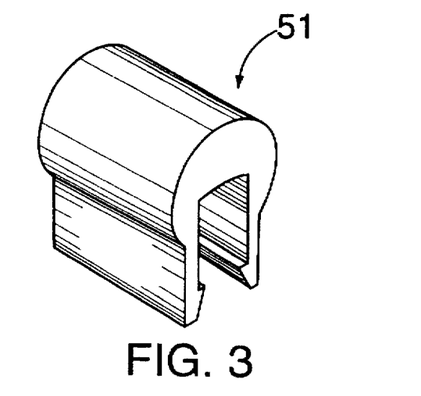
FIG. 3 is an isometric detail of a clip.
Figure 3A:
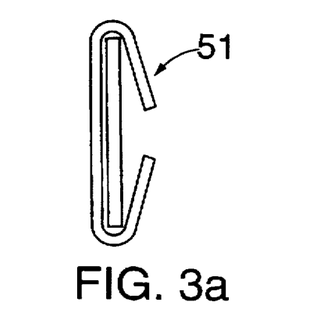
FIG. 3a is a side view of an alternative clip.

As depicted in FIG. 5, the extension unit 10 is initially placed over the post 50 such that the sides of the engaging surface and the retaining end of the post are approximately parallel. The extension unit 10 is then rotated until the engaging surface 15, as depicted in FIG. 6, engages the post, thus creating a sloppy fit. Then, a leaf from each of two adjacent extension units are placed end to end or, preferably, overlapping and are stabilized with the attachment of a clip 51. A detail of a typical clip is found in FIG. 3.

FIG. 6 is a schematic of one embodiment and demonstrates a sloppy fit of an engaging surface 15 of an extension unit 10 with a retaining end 50 of a post. In the embodiment schematically shown in FIG. 6, the cross section of the engaging surface defines an aperture which is square and slightly larger than a cross section of the square retaining end of the post. This difference in size of the aperture and the retaining end of the post provides for a sloppy fit. As demonstrated in FIG. 6, the extension unit engages the post snugly and movement is constricted in the position shown. However, as is clear from the schematic, a clockwise rotation of the extension unit will allow removal of the unit from the post. For added stability, the spaces between the post and the engaging surface can be filled with cement, especially where the modular foundation is to remain in place for an extended time.

Figures 2, 2A:
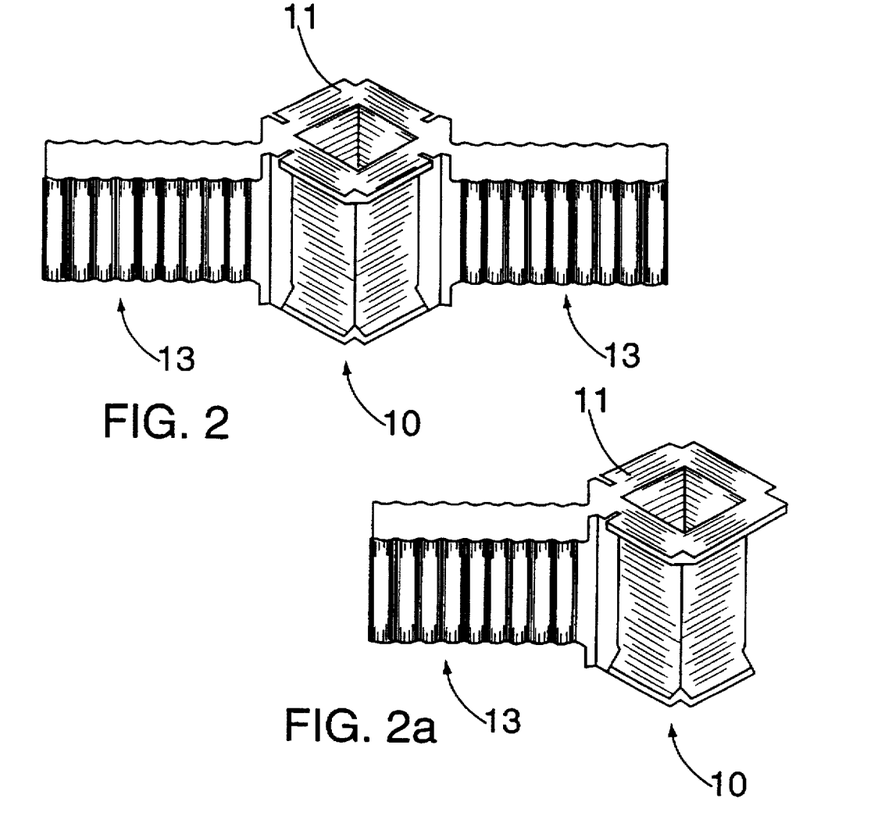
FIG. 2 is an isometric view of the embodiment of FIG. 1.
FIG. 2a is an isometric view of another embodiment of an extension unit with one leaf.
Figure 4:
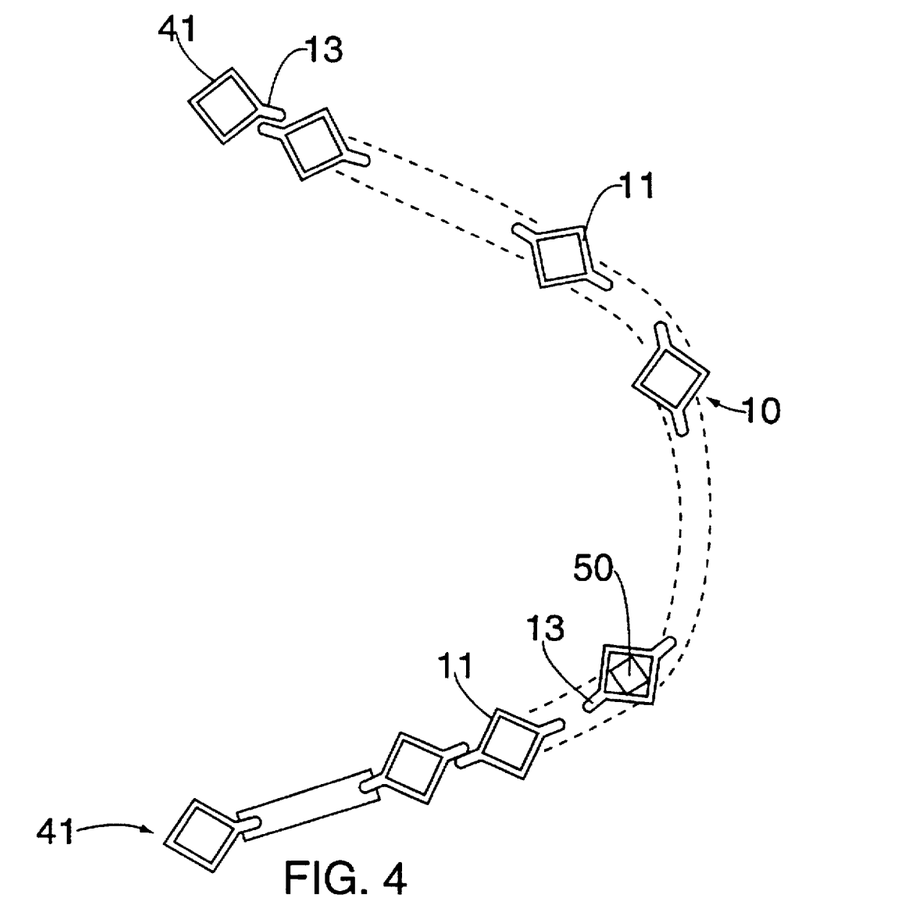
FIG. 4 is a schematic of a plan view of a dental bridge foundation for an entire jaw, formed by the interconnection of several modular extension units.

A schematic of a foundation of a dental bridge is shown in FIG. 4. At each end 41 of the foundation the modules have only one leaf. An example of an extension unit of a module with only one leaf is shown in FIG. 2a. In FIG. 4, leaves of extension units which overlap as well as leaves which substantially meet end to end, are shown.

Figure 8:
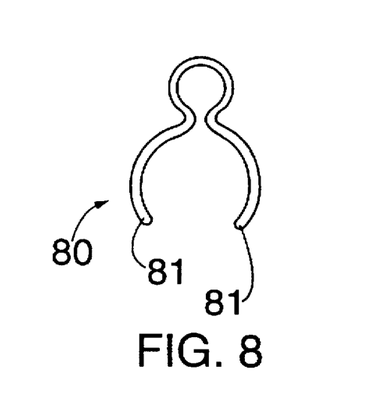
FIG. 8 is a side elevation view of a spring-loaded support skeleton.
Figure 9:
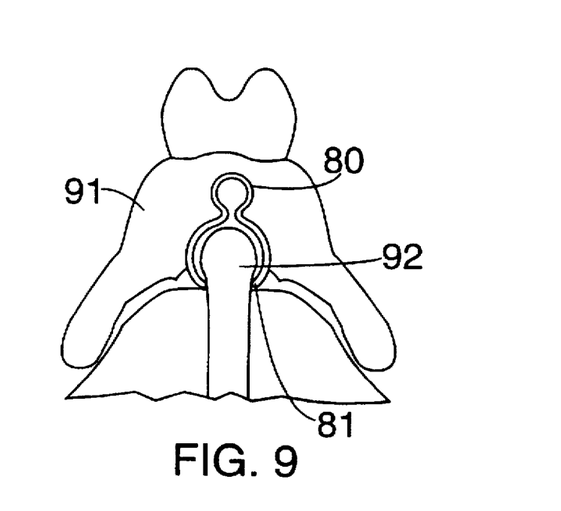
FIG. 9 is a schematic cross-section view of a cap being constructed over the spring-loaded support skeleton of FIG. 8 which has been placed over a post.

FIG. 8 is a plan view of a spring-loaded support skeleton, generally designated by the numeral 80, which is fitted on the post of FIG. 7. The spring of FIG. 8, as is depicted in FIG. 9, serves as a skeleton for the construction of a cap 91. The ends of the spring 81 engage the neck of the anchor post 92.

Figure 10A:
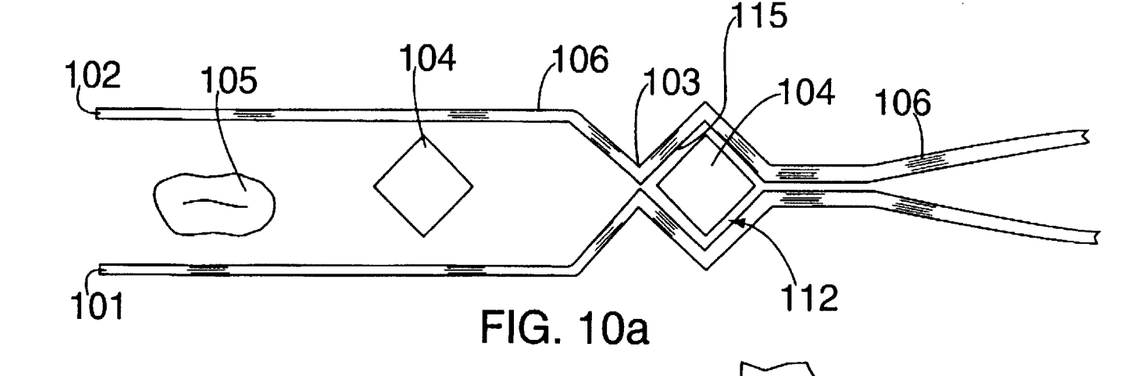
FIG. 10a is a schematic plan view of the in situ construction of the embodiment of FIG. 10.

As shown in FIGS. 10 and 10a another embodiment of this invention can be constructed in situ from two generally parallel extension leaves 101 and 102. FIG. 10a schematically demonstrates an intermediate stage in the construction of the foundation of the embodiment of FIG. 10. The first extension leaf unit 101 runs along the buccal side of the posts 104 and the tooth stubs 105, and the second extension leaf unit 102 runs along the lingual side of the posts 104 and tooth stubs 105. The extension units are joined together, as by crimping, at points 103 to form, e.g., the quadrilateral engaging surfaces 115, which surround and engage the posts 104 or the tooth stubs 105. The cross section of the engaging surfaces 115 defines the aperture 112. The intermediate leaves 106, between the corners 103 of the engaging surfaces 115 can be corrugated, by crimping and bending, as shown in FIG. 10, or left straight, as shown in FIG. 10a. The crimped and shaped extension leaves 101,102 can be secured together by, e.g., cementing, at the corners 103 of the engaging surfaces 115, or crimping at those corners, and/or at intermediate locations along the intermediate leaves.

When using the modular embodiment of FIGS. 1 and 7, the support posts 70 are screwed directly through the gum tissue and into the underlying bone matrix. A pilot hole can be drilled first, if desired and useful. An extension unit 10 can be placed over each of the anchored screw posts 70, forming a sloppy fit, and then slightly rotated to firmly engage the post 73 into the engaging surfaces 15. A leaf from each extension unit is then clipped together, locking the post head and engaging surface into the engaged position. Preferably, a spring-loaded support skeleton 80 is fitted over the post head, and a prosthesis is then constructed over the skeleton 80.

The drawings of FIGS. 11 through 17 reflect further preferred embodiments of this invention, which can be used to prepare a unitary, relatively rigid prosthesis foundation, in situ, which can be removably attached to and supported by implanted dental posts, in accordance with this invention. The support framework provides for supporting artificial teeth, and is attached to the underlying implanted anchor posts in a removable and reinsertable manner. This system provides means to accommodate the varying angles at which the posts are implanted into the jawbone, as a result of the well known divergences in shape of the jawbone, so that the buccal-to-lingual, and longitudinal, angular divergences of the implanted posts are overcome, such that the artificial teeth are supported in the desired common parallel position. As a further advantage, the structure of this embodiment provides for great compressive strength, without lateral stress, or torque, against the dental posts or the jawbone.

Figure 11:
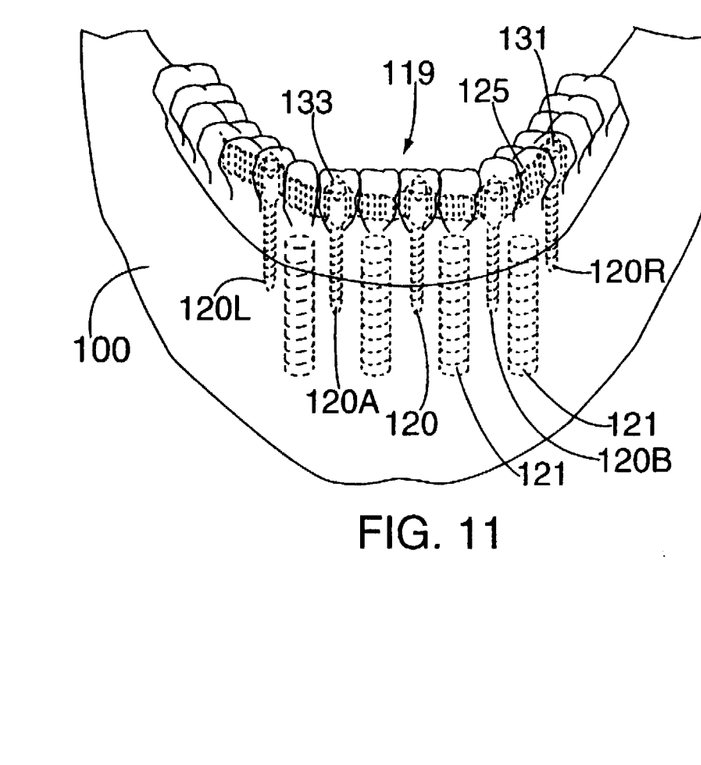
FIG. 11 is a schematic isometric view of a jaw including a front prosthetic formed from a rigid unitary foundation in accordance with the present invention.

FIG. 11 shows an overall schematic view of a jawbone having conventional hollow implants 121 in place and the externally threaded implanted dental posts 120, of this invention, also in place interspersed between and around the conventional posts 121. As shown, the dental posts 120 of this invention are threadedly embedded into the jawbone and support a dental prosthesis, generally indicated by the numeral 119, during healing of the wounds created by the implantation of the conventional implants 121, and while the implants 121 become secured to the jawbone 100.

Figures 12, 13, 14, 17:
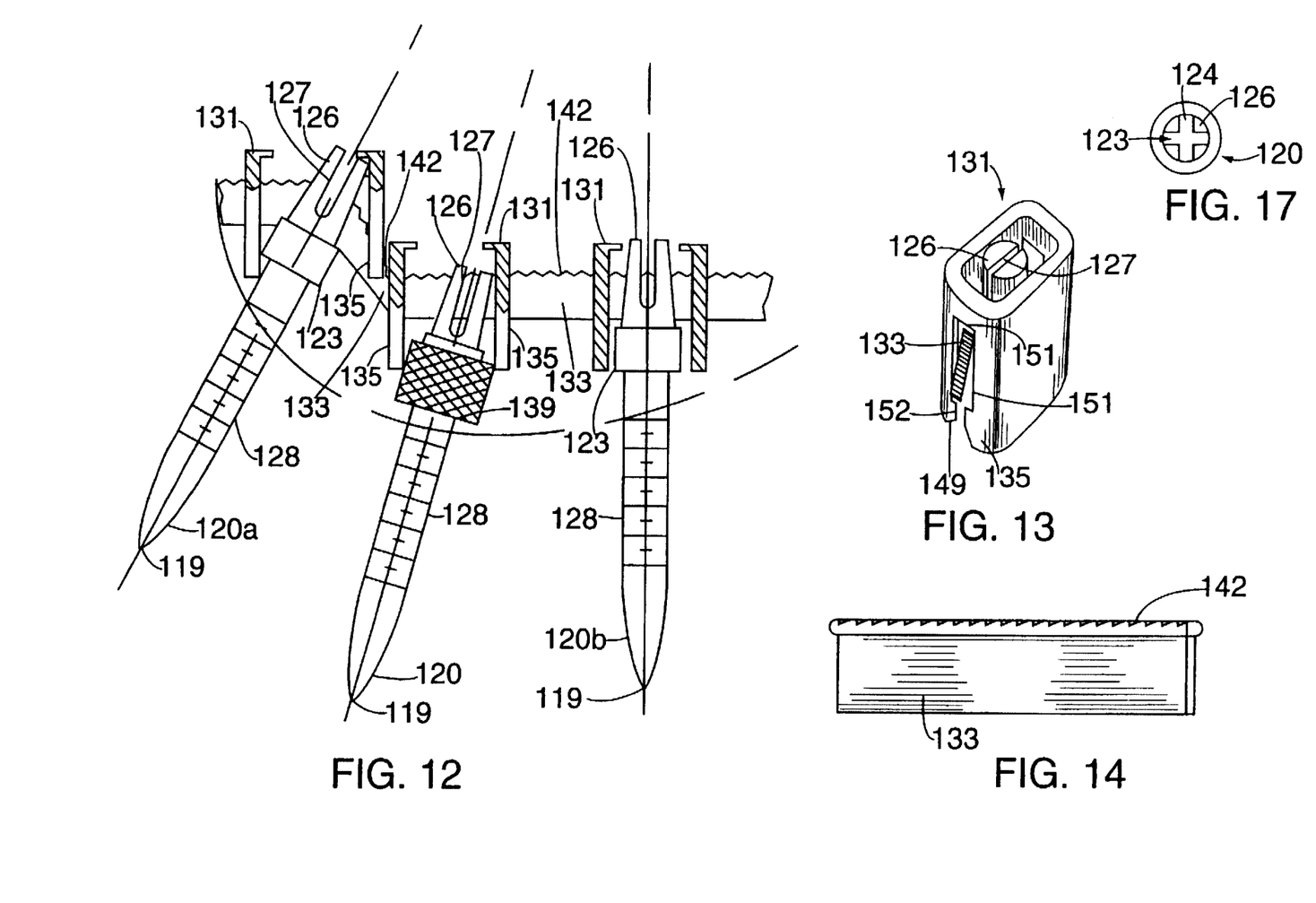

The dental posts 121 of this invention are shown in magnified views in FIG. 12. Three of the threaded posts 120, 120a, 120b are displayed in the divergent orientations, as they are in place in the jawbone. As shown, the posts 120 are not parallel to each other, but are askew, one to the other, both within the plane of the drawing and within a plane perpendicular to the drawing. As is shown, the implanted dental posts 120 have an externally threaded barrel portion 128 ending with a convergent pointed inner end 119; a squared off, or polygonal cross section, shoulder 123, and a convergent, but flat-topped outer head part 126. The convergent head part 126 has a lateral slot, defined by concave surface 127, passing through the head part 126. The connecting bar 133 in this embodiment is a continuous member, extending from the rightwardmost implanted post 120R through the intermediate posts 120b, 120, 120a, to the leftwardmost post 120L. The connecting bar 133 passes through the slot 127 in each of the posts.

Extending over each post head 126 and straddling the connecting bar 133 is a retaining cap, generally designated by the numeral 131. In FIG. 13, the retaining cap 131 is shown as a generally rectangular member having rounded corners; however, a cylindrical shape, or oblong cylindrical shape, can also be utilized. As shown, the retaining cap 131 fits over the post head 126 and locks against the polygonal shoulder 123 and the connecting bar 133. The lower portion of the retaining cap is split into two pairs of legs 135, providing a slot which straddles the connecting bar 133. In the most preferred embodiment shown in FIG. 13, the inner interior edges of the legs 152 are relatively close together, and the outer interior edges of the legs 151 are more widely separated, such that the connecting bar 133 fits loosely within the outer slot space defined by surfaces 151, but must be pushed between the lower surfaces 152, elastically pushing apart the legs 135 (to enter at chamfered corners 149) thereby locking the bar in place within the larger aperture 151 when the legs spring back.

In another embodiment shown in FIG. 17, the slot 123 at the top of the dental post 120 is cruciform, making less critical the orientation of the dental posts, reducing the need to excessively bend the connecting bar 133 in order to have it pass through an available slot.

As before, the relatively loose, or "sloppy", fit of the retaining cap 131 relative to the upper portion 126 of the dental post 120, permits each post 120 to be skewed relative to the retaining cap and to each other, while the retaining caps 131 on the several posts remain substantially in parallel. The parallel positioning of the retaining caps 131 is secured, in this preferred embodiment, by the interaction of the notches formed on the upper surface 142 of the connecting bar 133, with an edge of the retaining cap. Thus, in fitting this system into the mouth, the connecting bar 133 is threaded through the slots 127 of the several posts 120, and the retaining caps 131 are then placed over the post head 126, pivoted into mutually parallel orientations, and locked in place by inserting the inner surface edge 151 of the retaining cap 131 into a notch 142 of the connecting bar 133.

Figure 12A:
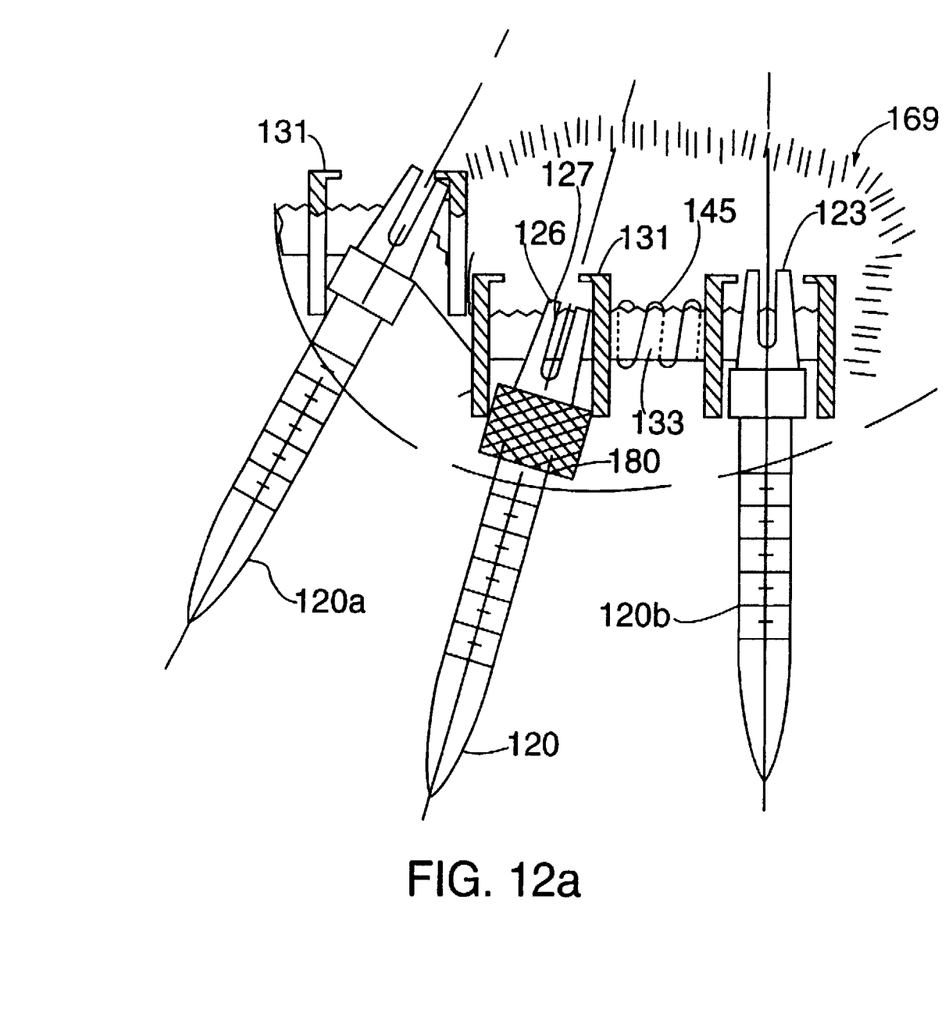
FIG. 12a is a further magnified view of the three dental posts from FIG. 12, including, in addition, a connecting bar and encapsulating compound.

As a further means of maintaining the relative orientation of the various parts of the foundation, a curable, malleable plastic material is applied over the entire assembly formed by the connecting bar 133, and retaining caps 131, as is shown in FIG. 12a. The malleable plastic is then cured into a relatively rigid matrix 160, firmly securing the relative orientations of the retaining caps 131 and connecting bar 133 relative to the slots 127 in the dental posts 120. By placing casements 139 around the post shoulders 123, to cover the inner end opening into the interior of the retaining caps 131, and a rectangular plug or casing 153, over the slot opening 151, the malleable plastic is prevented from entering inside of the retaining caps, thus keeping clear the slotted heads of the posts, and permitting ready removal of the caps and the connecting bar therefrom; and once the malleable plastic is cured to form a unitary rigid member, the rigid system can be readily removed from, and replaced onto, the posts, as the relative positions and orientations are locked.

Once the system is encased in the hardened plastic, artificial teeth of the desired size and color can be secured to the prosthetic foundation, so as to provide an immediate, though temporary, yet fully functioning dental prosthesis.

When preparing the unitary prosthesis of FIGS. 11 through 10, the dental posts 120 are threadedly implanted into the jawbone in the manner described above for the earlier modular embodiments. Alternatively, these posts can also be secured into any internally threaded, permanently installed, conventional osseo-integrated implants 121, of the type shown empty in FIG. 11. The connecting bar 133, either in interconnected shorter lengths, or as a continuous flexible length, can be inserted into the slots 127. This connecting bar can be made of any suitable dentally approved material, such as stainless steel, titanium or a synthetic flexible polymer, such as Mylar, and preferably has notches 142 formed along at least one long edge. The connecting bar should extend slightly beyond the terminal posts at each end, i.e., posts 120R and 120L, so that it can subsequently be secured in place.

The retaining caps 131 are then emplaced over each of the posts 120, such that the connecting bars 133 are straddled by the elastic legs 135 of the caps. The caps are placed in relative parallel orientation to each other, and then secured in that position by being pressed down until the outer edges of the slots 151 lock into the notches 142 of the connecting bar. As stated earlier, the caps are relatively loosely fitted over the posts 120; the caps 131 thus need not follow the angular orientation of the posts, thus the caps 121 can accommodate the angular divergences among the several posts, while maintaining relative parallel orientation among the caps.

The elastic legs 135 grip the connecting bar 133 to prevent accidental removal of the cap. The cap is thus positioned at the desired parallel orientations, and restrained in place by the grooves of the rectangular connecting bar 133.

The slots 127 are wider than the thickness of the connecting bar 133, to permit the bar to be pivoted about the buccal/lingual axis, relative to the post 120. The slot widths are preferably at least about 20% wider, and most preferably about 100% wider, than the thickness of bar 133.

To further immobilize the foundation structure, a layer of a plastic curable material is applied, covering the connecting bar 133 and the retaining caps 131, and then cured, or otherwise hardened, to form a unitary matrix structure 169. Casements are secured at the sides and bottoms of the retaining caps 131, so as to avoid the infiltration of the plastic material into the interior of the caps, which could cause an undesired interconnection between the retaining caps 131 and the implant posts 120. The encasing polymer can be any dentally approved thermoplastic or thermoset polymer, such as a methyl methacrylate, conventional dental composition, or other light-curing or self-curing acrylic, or other materials. If desired, the polymer can be applied in two layers, a first thin layer being applied, and then the structure is checked for uniformity and fit; if satisfactory, a final thicker rigid coating is applied to assure the formation of a rigid unitary structure.

To further enhance the structural strength of the unit, a coil can be placed over the connecting bar 133 intermediate the several retaining caps 131, to act as a form for holding the curable composition in place before curing, and to act as reinforcing members in the final cured structure. As shown in FIG. 12a, a coil can be placed so as to drape over the connecting bar and the polymer is then pushed between and around the coils and then cured. A U-shaped coil of FIG. 17 can be formed from a conventional helical coil, which is then pressed at a given location so as to form a U-shaped trough along each of the coils.

Figures 18, 19:
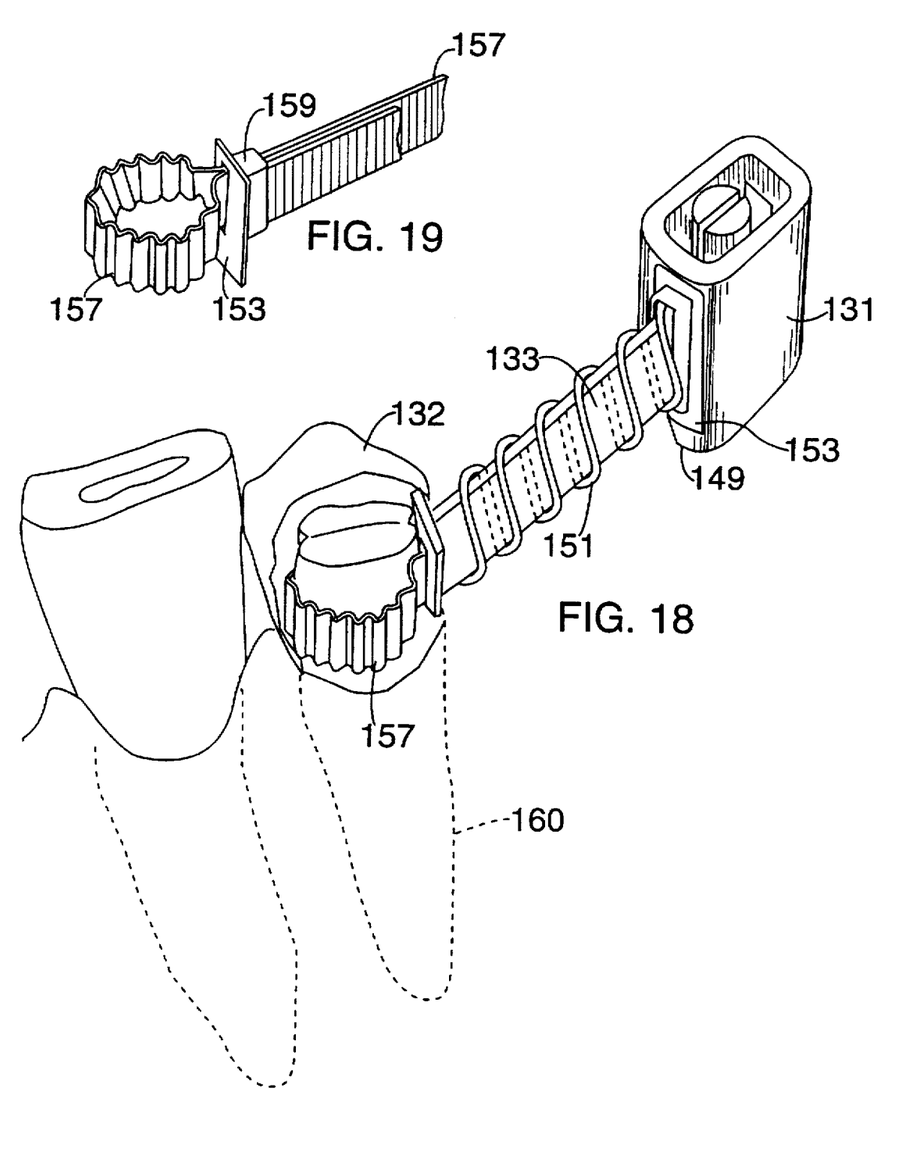
FIG. 18 is an isometric sketch showing an embodiment where the terminal support post is a tooth stub.
FIG. 19 is an isometric sketch of the wrapping means for securing a prosthesis foundation to a prepared tooth stub.

In the further preferred embodiment, shown in FIG. 18, the connecting bar 133 is threaded through a series of spring coils 151 and plug sheaths 153, the ends of each spring coil 153 are secured into the rectangular casement sheaths 153 which fit securely around the connecting bar 133 and are pressed by the coil against the legs 135 and over the slot between the legs 135 of the caps 131, so as to prevent the passage of substantial amount of the curable composition into the interior of the cap 131, and into contact with the posts 120. At the chamfered corners 149, which are not covered by the plug sheath 153, the matrix serves to lock the legs 135 together. The presence of curable composition within the cap, could result in a bonding between the post 120 and the surrounding cap 131, thereby interfering with the removability of the prosthesis foundation from the dental posts.

The coil 145 can be formed preferably of titanium or stainless steel, or from an elastic, dentally approved, polymeric material. The connecting bar 133 can be formed again of titanium or stainless steel, or of a strong, but flexible polymer, such as Mylar. After the prosthesis is formed in the mouth of the patient, and the encasing polymer has hardened, the prosthesis can be removed from the support posts, and artificial teeth secured along the prosthesis foundation by known methods, to result in the desired temporary dental prosthesis.

The connecting bar 133 can also be formed in shorter unit lengths interconnected between immediately adjacent implanted posts 120, and locked and secured together, as by crimping or clipping, before being encased in the curable plastic matrix.

The dental posts can be formed of various thread sizes and diameters, including those which are suitable for insertion into the permanent type osseo-integrated implants 121.

Figure 15:
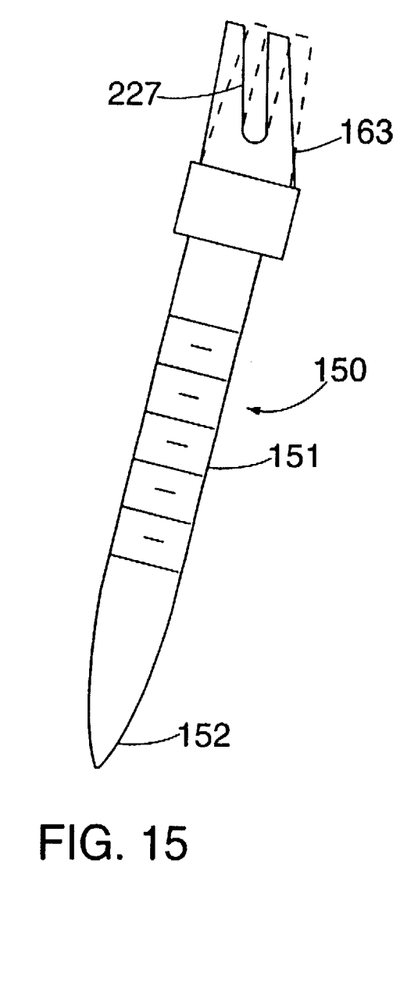
FIG. 15 is a side elevation view of an alternative embodiment of a dental post having a bendable upper portion.
Figure 16:
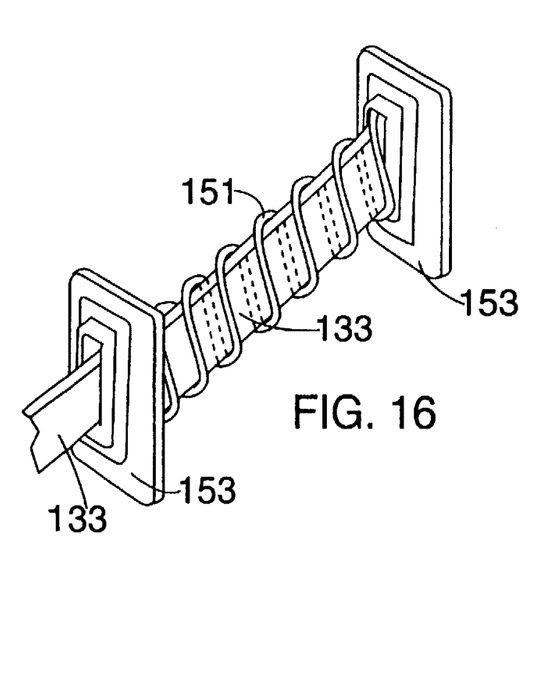
FIG. 16 is a magnified cut-away view of the coil-threaded connecting bar extending between two slotted caps.

As a further embodiment of the dental posts of this invention, shown in FIG. 15, the post generally designated by the numeral 150, has a conventional threaded barrel 151 and a convergent inner end point 152. The slotted head 163, however, is formed so as to be plastically bendable relative to the stock 151 after implantation, using a keyed wrench having an internal tongue to fit into the slot 227 and a surrounding flange to fit around the post head and the upper edge of the polygonal shoulder 123. This permits a further means for accommodating any excessive angular divergence from the perpendicular of an implanted dental post, as a result of unusual formations of the jawbone. The bendable slotted outer end portion 153, thus works together with the sloppy fit of the retaining caps 131 and the connecting bar 133, to ensure a parallel orientation for the caps so as to form a more firm and straight support for the artificial teeth.

Figure 20:
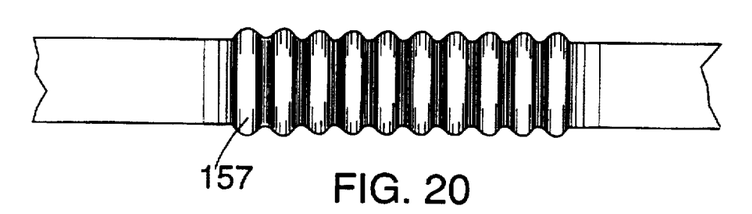
FIG. 20 is a magnified close-up view of a portion of the wrapping means for securing the prosthesis to a tooth stub.

In the embodiment depicted in FIGS. 19 through 21, the terminal point for the foundation support is a prepared tooth stub 160. The stub 160 is secured by the strap 157, to the foundation structure. The rectangular plug 153 at the terminal position adjacent the tooth stub, provides a collar 159 for holding the end of the connecting bar 133 and the ends of the flexible holding strap 157, when the strap 157 is wrapped around the tooth stub. The collar 159 of the rectangular plug 153, is then crimped so as to hold the connecting bar and the two ends of the strap 157 in place. In this preferred situation, a cap 132 is also placed over the tooth stub and surrounding the flexible strap 157. Preferably, the thin, flexible strap is made of, for example, a strong polymeric material such as Mylar or a flexible metal such as titanium or stainless steel, and is corrugated. The corrugation allows for easy expansion around the stub and further permits space for the soft curable plastic to flow around the tooth. To avoid adhesion of the curable plastic to the tooth stub, known lubricants are applied to the tooth stub.

The coil 151 can have spring-like resilience, to enable it to be readily expanded or compressed to fit between two adjacent caps, regardless of the spacing between the adjacent implanted posts, and/or tooth stubs. Although, of course, it is undesirable to have a spring-load consistently acting against an implanted post, it is noted that when the polymer is cured to form the rigid encasement, all spring pressure is eliminated.

It has been found that the unitary structure of this prosthetic device, provides great compressive strength for the unit while avoiding any lateral stress or torque which might loosen the implanted posts in the jawbone, or even crack the jawbone. The locked together structure can then be readily removed and replaced.

What is claimed is:

1. A modular foundation for a rigid prosthetic dental bridge, said foundation comprising a plurality of modules, each module comprising one each of (a) a post and (b) an extension unit, said post having a first anchor end, adapted to anchor said post into rigid dental material selected from the group consisting of tooth stubs and bone matrix, and a second retaining end, for engaging and supporting the extension unit; said extension unit comprised of (i) at least one engaged support and (ii) no more than two leaves extending from said engaged support in a direction transverse to said post, each said leaf being selectable by length, said engaged support having a portion so sized and shaped so as to maintain a sloppy fit with the retaining end of said post, said sloppy fit permitting a minor, constrained degree of rotation of said extension unit with respect to said retaining end of said post; said extension unit of one module adapted to couple with at least one other adjacent module.

2. The modular foundation of claim 1, wherein the anchor end comprises an externally threaded outer surface.

3. The modular foundation of claim 1, wherein at least one module comprises, in addition, at least one spring loaded support skeleton, and said spring loaded support skeleton being resiliently supported by the retaining end of the post.

4. A method of forming a foundation for a rigid prosthetic bridge, utilizing a module, said foundation being formed from a series of at least two modules, each module comprising (a) a post and (b) an extension unit; said post comprising a first anchor end and a second retaining end; the extension unit comprising an engaged support, and at least one leaf extending outwardly from the engaged support; the method comprising anchoring the anchor end of a first post in bone matrix or a tooth stub; engaging the retaining end of said first post in a sloppy fit with the engaged support of a first extension unit, said sloppy fit permitting a minor, constrained degree of rotation of said extension unit with respect to said retaining end of said first post; anchoring the anchor end of a second post in adjacent bone matrix or an adjacent tooth stub; engaging the retaining end of said second post in a sloppy fit with a second extension unit; coupling one leaf of the first extension unit to one leaf of the second extension unit such that the extension units are both rotated so that they both are wedged against their respective posts and the two extension units are coupled together so as to maintain the wedged juxtapositions of the retaining ends and the engaging means, thus forming a rigid unit to extend over the entire length of the desired prosthetic bridge to be constructed, forming a foundation for prosthetic caps.

5. A method in accordance with claim 4, wherein at least one screw ended post is anchored in bone matrix or a tooth stub adjacent to another anchored post or a tooth stub, to form a series of anchored perpendicular support elements in the mouth of the patient; placing a first extension unit along the buccal side of the series of the anchored perpendicular support elements, placing a second extension unit along the lingual side of the anchored perpendicular support elements and extending generally parallel to said first extension unit, joining the first and second extension units together at locations intermediate the anchored perpendicular support elements, so as to form engaging surfaces surrounding the anchored perpendicular support elements, thus locking the anchored perpendicular support elements together into a rigid structure, and constructing dental prostheses over the rigid structure.

* * * * *